(12) United States Patent
Matsumoto (10) Patent No.: US 10,589,420 B2
(45) Date of Patent: Mar. 17, 2020

(54) HAND DEVICE

(71) Applicant: Fanuc Corporation, Yamanashi (JP)

(72) Inventor: Ryou Matsumoto, Yamanashi (JP)

(73) Assignee: Fanuc Corporation, Yamanashi (JP)

( * ) Notice: Subject to any disclaimer, the term of this patent is extended or adjusted under 35 U.S.C. 154(b) by 208 days.

(21) Appl. No.: 15/711,668

(22) Filed: Sep. 21, 2017

(65) Prior Publication Data

US 2018/0085916 A1 Mar. 29, 2018

(30) Foreign Application Priority Data

Sep. 29, 2016 (JP) ................................ 2016-191537

(51) Int. Cl.
| | | |
|---|---|---|
| *B25J 9/06* | (2006.01) | |
| *B25J 15/00* | (2006.01) | |
| *B23P 19/04* | (2006.01) | |
| *B25J 9/00* | (2006.01) | |
| *B25J 9/04* | (2006.01) | |
| *B25J 9/10* | (2006.01) | |

(Continued)

(52) U.S. Cl.
CPC ................. *B25J 9/06* (2013.01); *B23P 19/04* (2013.01); *B25J 9/0096* (2013.01); *B25J 9/046* (2013.01); *B25J 9/1045* (2013.01); *B25J 9/1612* (2013.01); *B25J 15/0019* (2013.01); *B25J 15/0052* (2013.01); *B04B 2013/006* (2013.01); *G01N 35/0099* (2013.01)

(58) Field of Classification Search
CPC ................ B25J 15/0009; B25J 15/0014; B25J 15/0019; B25J 11/0095; B25J 9/06; B25J 9/1612; B25J 15/0052; B25J 9/046; B25J 9/1045; B25J 9/0096; B23P 19/04; B04B 2013/006; G01N 35/0099

See application file for complete search history.

(56) References Cited

U.S. PATENT DOCUMENTS

| | | |
|---|---|---|
| 5,172,951 A | 12/1992 | Jacobsen et al. |
| 5,328,224 A | 7/1994 | Jacobsen et al. |

(Continued)

FOREIGN PATENT DOCUMENTS

| | | |
|---|---|---|
| CN | 104551629 A | 4/2015 |
| CN | 105818156 A | 8/2016 |

(Continued)

OTHER PUBLICATIONS

Japan Patent Office, Office Action dated Oct. 16, 2018 for Japan Patent Application No. 2016-191537.

(Continued)

*Primary Examiner* — Stephen A Vu
(74) *Attorney, Agent, or Firm* — Winstead PC (57) ABSTRACT

A hand device includes: a first hand fixed to a robot arm; a second hand that has a workpiece stage on which a workpiece is placed and that is coupled to the first hand; a positioning mechanism that positions the second hand relative to the first hand when the second hand is to be coupled to the first hand; and a coupling mechanism that couples the second hand having been positioned by the positioning mechanism to the first hand, and uncouples the second hand from the first hand, wherein the hand device is configured to clamp the workpiece between the first hand and the second hand by moving at least a part of the first hand toward the second hand.

10 Claims, 12 Drawing Sheets

(51) Int. Cl.
*B25J 9/16* (2006.01)
*B04B 13/00* (2006.01)
*G01N 35/00* (2006.01)

(56) References Cited

U.S. PATENT DOCUMENTS

| | | |
|---|---|---|
| 5,588,688 A | 12/1996 | Jacobsen et al. |
| 8,882,437 B2 * | 11/2014 | Nakanishi ............ B65G 49/061 |
| | | 294/902 |
| 9,004,560 B2 * | 4/2015 | Umeno ................ B25J 15/0033 |
| | | 294/119.1 |
| 2009/0315281 A1 | 12/2009 | Tuauden et al. |
| 2010/0314895 A1 | 12/2010 | Rizk et al. |
| 2015/0098790 A1 * | 4/2015 | Wakabayashi .... H01L 21/67742 |
| | | 414/805 |
| 2015/0119214 A1 | 4/2015 | Sasaki |
| 2015/0132086 A1 * | 5/2015 | Saito ................ H01L 21/67178 |
| | | 414/222.13 |
| 2015/0170954 A1 * | 6/2015 | Agarwal ........... H01L 21/68757 |
| | | 414/226.05 |
| 2015/0179491 A1 * | 6/2015 | Katsuda ................ B25J 9/1694 |
| | | 700/213 |
| 2016/0214262 A1 | 7/2016 | Saito et al. |
| 2016/0375532 A1 | 12/2016 | Sasaki |

FOREIGN PATENT DOCUMENTS

| | | |
|---|---|---|
| EP | 0470458 A1 | 2/1992 |
| JP | S58-154088 U | 10/1983 |
| JP | S60-020882 A | 2/1985 |
| JP | S63-147284 U | 9/1988 |
| JP | S64-046735 U | 3/1989 |
| JP | H05-208388 A | 8/1993 |
| JP | H06-079680 A | 3/1994 |
| JP | 2000-272749 A | 10/2000 |
| JP | 2009-544476 A | 12/2009 |
| JP | 2013-233650 A | 11/2013 |
| JP | 2016-013583 A | 1/2016 |
| WO | WO-9601724 A1 | 1/1996 |

OTHER PUBLICATIONS

Japan Patent Office, Search Report dated Oct. 11, 2018 for Japan Patent Application No. 2016-191537.

* cited by examiner

HAND DEVICE

CROSS-REFERENCE TO RELATED APPLICATIONS

This application is based on and claims priority to Japanese Patent Application No. 2016-191537 filed on Sep. 29, 2016, the entire content of which is incorporated herein by reference.

TECHNICAL FIELD

The present invention relates to a hand device that is used by being attached to a robot arm.

BACKGROUND ART

A known hand device of this type grabs a workpiece with a pair of opening-closing claws that are attached to a distal end of a robot arm (e.g., see PTL 1). The workpiece grabbed by this hand device is disposed at a position for a process by operation of the robot arm, and the workpiece undergoes a predetermined process while being grabbed by the hand device.

CITATION LIST

Patent Literature

{PTL 1}
Japanese Unexamined Patent Application, Publication No. 2013-233650

SUMMARY OF INVENTION

A hand device of a first aspect of the present invention includes: a first hand fixed to a robot arm; a second hand that has a workpiece stage on which a workpiece is to be placed and that is to be coupled to the first hand; a positioning mechanism that positions the second hand relative to the first hand when the second hand is coupled to the first hand; and a coupling mechanism capable of coupling the second hand having been positioned by the positioning mechanism to the first hand, and also capable of uncoupling the second hand from the first hand, wherein the hand device is configured to clamp the workpiece between the first hand and the second hand by moving at least a part of the first hand toward the second hand.

DESCRIPTION OF EMBODIMENTS

A hand device 1 according to a first embodiment of the present invention will be described below with reference to the drawings.

Figure 1:
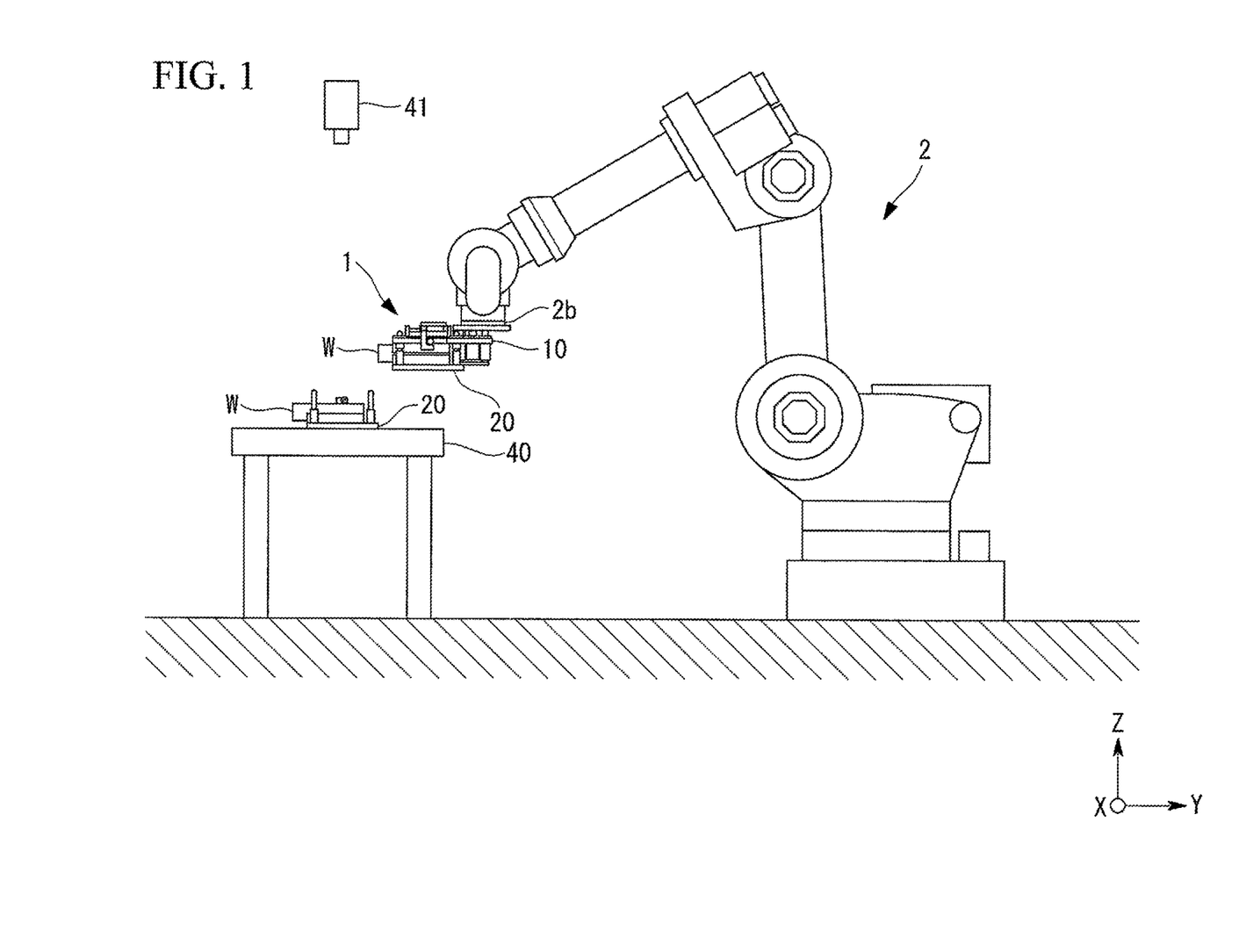
FIG. 1 is a schematic front view of a hand device and a robot arm according to a first embodiment of the present invention.

As shown in FIG. 1, the hand device 1 includes a first hand 10 fixed to a robot arm 2, and a second hand 20 to be coupled to the first hand 10.

The robot arm 2 to which the first hand 10 is fixed includes a plurality of movable parts, and a plurality of servomotors 2a that respectively drive the plurality of movable parts. At a distal end of the robot arm 2, a mount 2b to which the first hand 10 is attached is provided.

Any type of servomotor, such as a rotary motor or a linear motor, can be used as the servomotors 2a. Each servomotor 2a has a built-in operation position detector, such as an encoder, that detects the operation position, and a detection value of this operation position detector is sent to a robot control unit 30.

Figure 2:
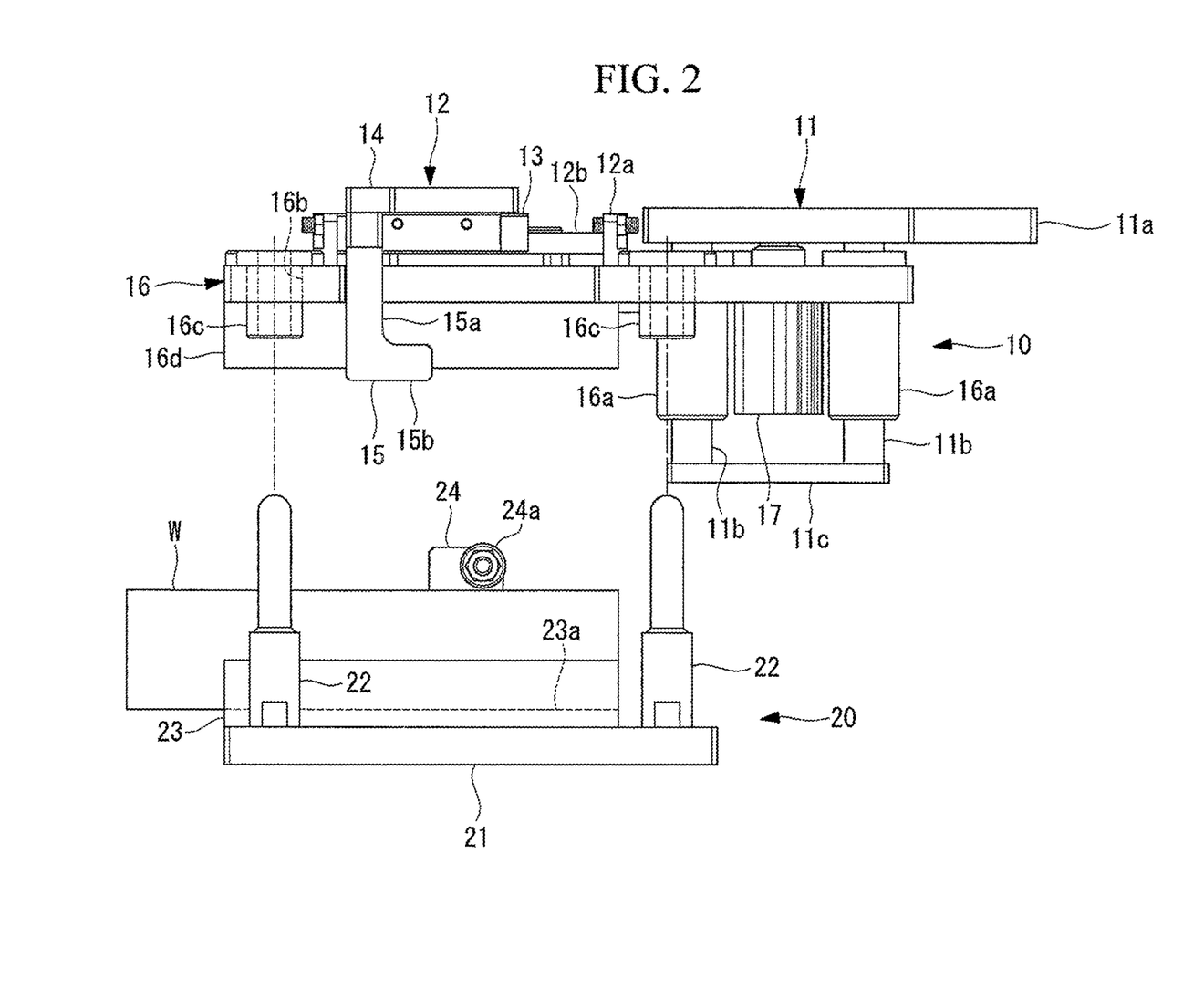
FIG. 2 is a front view of the hand device of the first embodiment.
Figure 3:
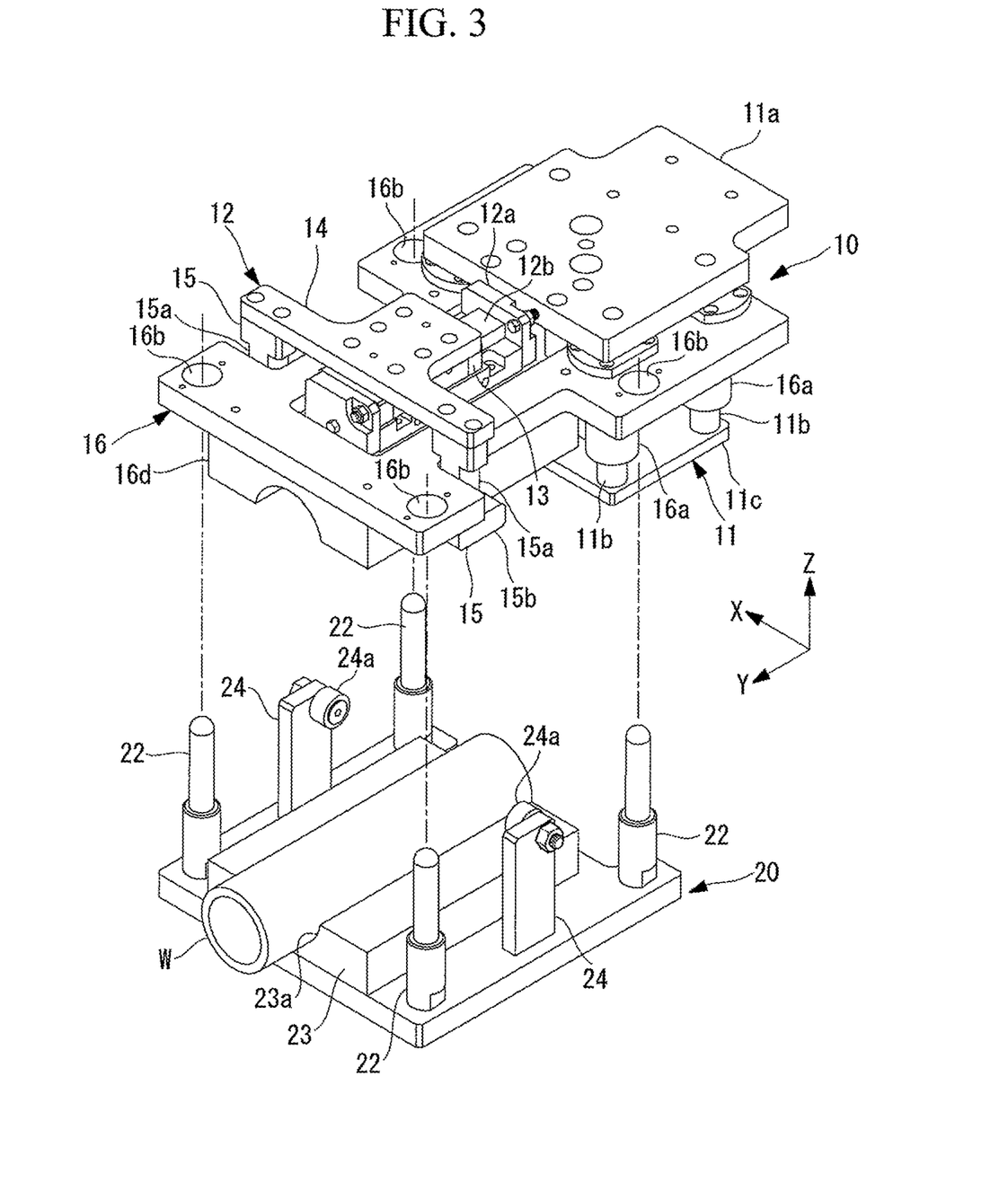
FIG. 3 is a perspective view of the hand device of the first embodiment.

As shown in FIG. 2 and FIG. 3, the first hand 10 has a base 11 that is fixed to the mount 2b of the robot arm 2. The base 11 has: a fixed plate 11a that is fixed to the mount 2b with bolts (not shown); a plurality of guide shafts 11b extending from the fixed plate 11a in a plate thickness direction of the fixed plate 11a (in this embodiment, extending downward); and a reinforcing plate 11c to which lower ends of the plurality of guide shafts 11b are fixed. In the following description, the plate thickness direction will be referred to as a vertical direction or a Z-axis direction.

A coupling mechanism 12 is fixed to the fixed plate 11a of the base 11. The coupling mechanism 12 has: a base member 12a that is fixed to the fixed plate 11a by welding, bolts, etc.; an engaging member driving device 13, such as an air cylinder or a linear motor, that is fixed to the base member 12a; and a first engaging member 14 that is supported on a rail 12b provided on the base member 12a so as to be movable in a predetermined direction, and that is moved along the rail 12b by the engaging member driving device 13. In this embodiment, the predetermined direction is a Y-axis direction orthogonal to the Z-axis direction, and a direction orthogonal to the Z-axis direction and the Y-axis direction will be referred to as an X-axis direction.

The first engaging member 14 has a pair of engaging pieces 15 that are arranged in the X-axis direction with an interval, and each engaging piece 15 has a vertically extending portion 15a extending in the vertical direction, and a horizontally extending portion 15b extending in a horizontal direction (in this embodiment, the Y-axis direction) from a lower end side of the vertically extending portion 15a.

The first hand 10 further has a movable member 16 that is supported by the plurality of guide shafts 11b so as to be movable in the vertical direction relative to the base 11, and a driving device for clamping 17, such as an air cylinder or a linear motor, that is fixed to the base 11 and the movable member 16 and moves the movable member 16 in the vertical direction relative to the base 11.

A plurality of guide bushes 16a respectively fitted on the plurality of guide shafts 11b are fixed to the movable member 16, so that the movable member 16 can move in the vertical direction along the guide shafts 11b.

The movable member 16 is provided with a plurality of through-holes 16b, and the through-holes 16b extend through the movable member 16 in the vertical direction. The through-holes 16b are disposed at positions in the horizontal direction different from positions of the plurality of guide bushes 16a, and a guide bush 16c is also provided inside each of the through-holes 16b.

As shown in FIG. 2 and FIG. 3, the second hand 20 has a plate-shaped second hand main body 21, a plurality of guide shafts 22 extending upward from the second hand main body 21, and a workpiece stage 23 provided on an upper surface of the second hand main body 21. The guide shafts 22 are disposed at positions respectively corresponding to the through-holes 16b of the movable member 16 of the first hand 10. For example, the workpiece stage 23 is made of a plastic material, such as MC nylon, and a recess 23a corresponding to the shape of a workpiece W is formed in an upper surface of the workpiece stage 23.

The second hand 20 has a pair of second engaging members 24 that are provided on the second hand main body 21 to be arranged in the X-axis direction with an interval. In FIG. 2, the second engaging member 24 on the near side is not shown. The second engaging members 24 are provided so as to extend upward from the second hand main body 21, and an engaging portion 24a protruding from the second engaging member 24 in the horizontal direction is provided at an upper end of each second engaging member 24. In this embodiment, the engaging portion 24a is a shafted bearing called cam follower. The shaft is fixed to the upper end of the second engaging member 24, and the outer ring of the bearing functions as the engaging portion 24a. In this embodiment, the position of the engaging portions 24a in the Y-axis direction corresponds to a substantially central position of the workpiece stage 23 in the Y-axis direction, and the pair of second engaging members 24 are disposed one on each side of the workpiece stage 23 in the X-axis direction.

The engaging member driving device 13 and the driving device for clamping 17 are connected to the robot control unit 30, and the engaging member driving device 13 and the driving device for clamping 17 are configured to be controlled by the robot control unit 30.

Figure 4:
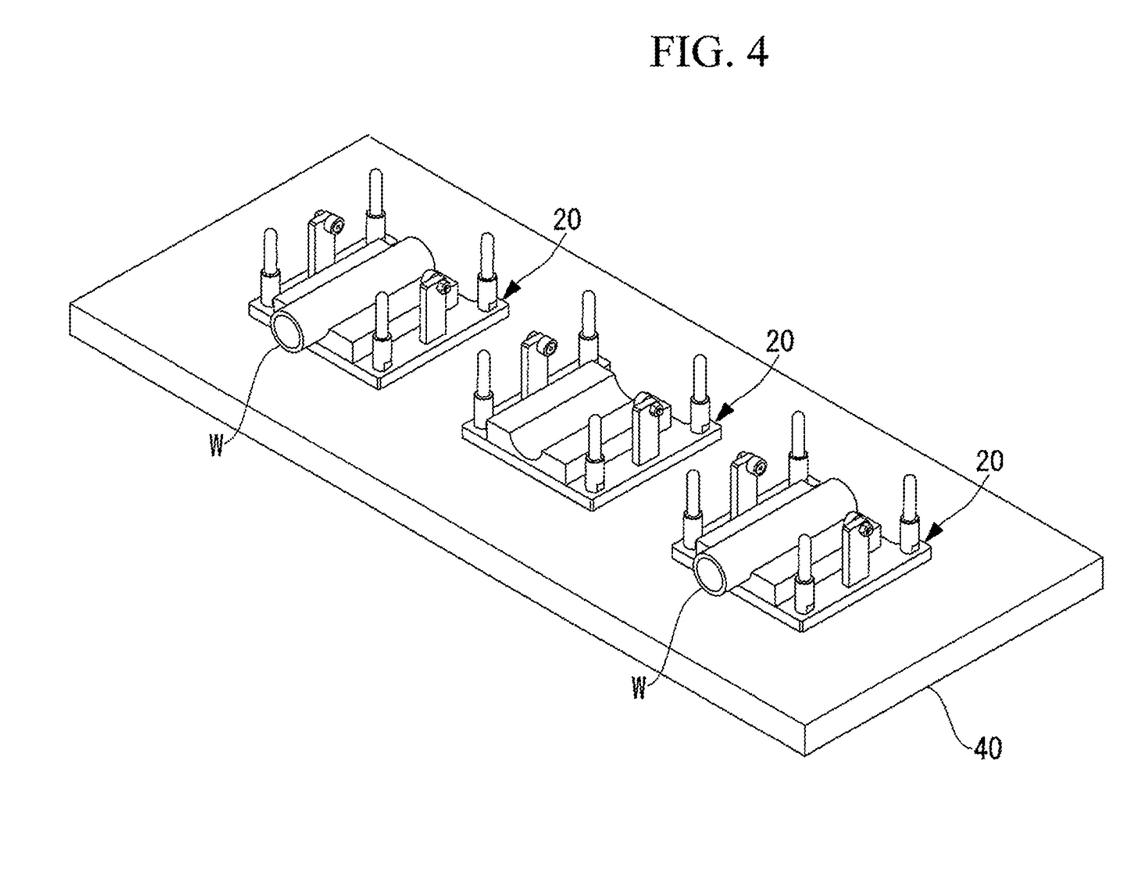
FIG. 4 is a perspective view of a second hand of the hand device of the first embodiment.

As shown in FIG. 4, in this embodiment, a plurality of second hands 20 are mounted on a table 40, and the workpiece W is placed in each second hand 20 by an operator or a robot (not shown).

Figure 5:
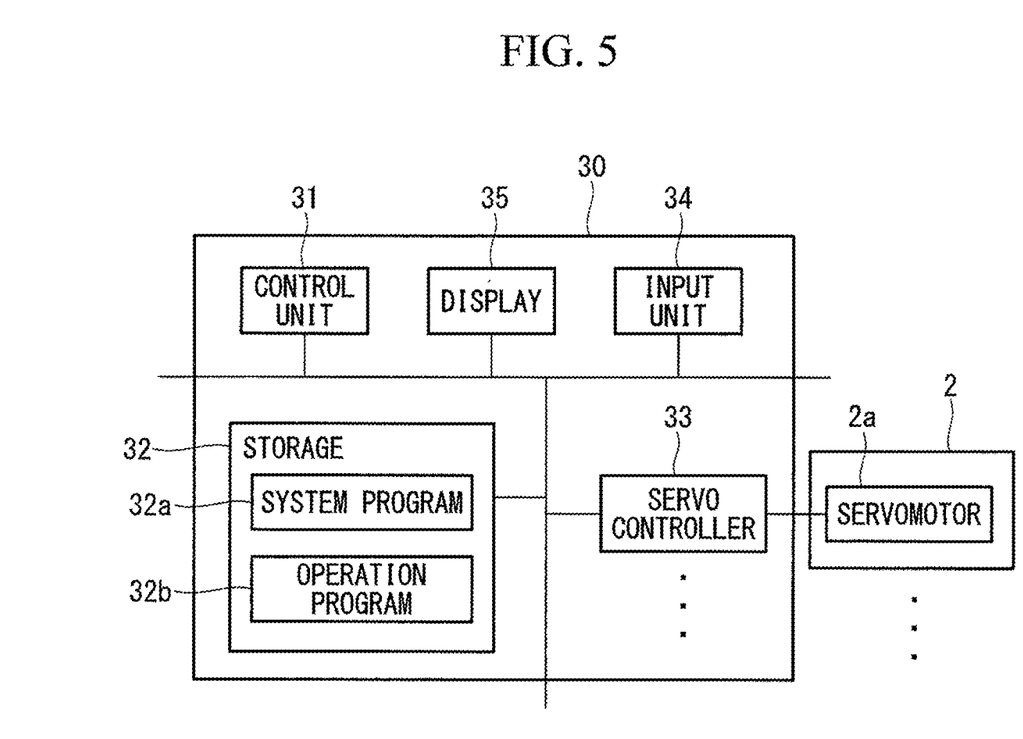
FIG. 5 is a block diagram of a robot control unit of the first embodiment.

As shown in FIG. 5, the robot control unit 30 includes: a controller 31 that is a computer having a CPU, RAM, ROM, etc.; a non-volatile storage 32; a plurality of servo controllers 33 provided so as to respectively correspond to the plurality of servomotors 2a; an input unit 34 that is manipulated, for example, to create an operation program of the robot arm 2; and a display 35. Each servo controller 33 has a processor and a storage, such as a ROM or RAM, and sends a driving signal to a servo amplifier of each servomotor 2a to control the operation position, operation speed, etc. of each servomotor 2a.

A system program 32a is stored in the storage 32, and the system program 32a is responsible for the basic functions of the robot control unit 30. In addition, at least one operation program 32b created using the input unit 34, for example, is stored in the storage 32. For example, the controller 31 of the robot control unit 30 is operated through the system program 32a. The controller 31 retrieves the operation program 32b stored in the storage 32, and temporarily stores the operation program 32b in the RAM. Then, the controller 31 sends a control signal to the servo controllers 33, the engaging member driving device 13, and the driving device for clamping 17 in accordance with the retrieved operation program 32b, and thereby controls the servomotors 2a, the engaging member driving device 13, and the driving device for clamping 17.

Figure 6:
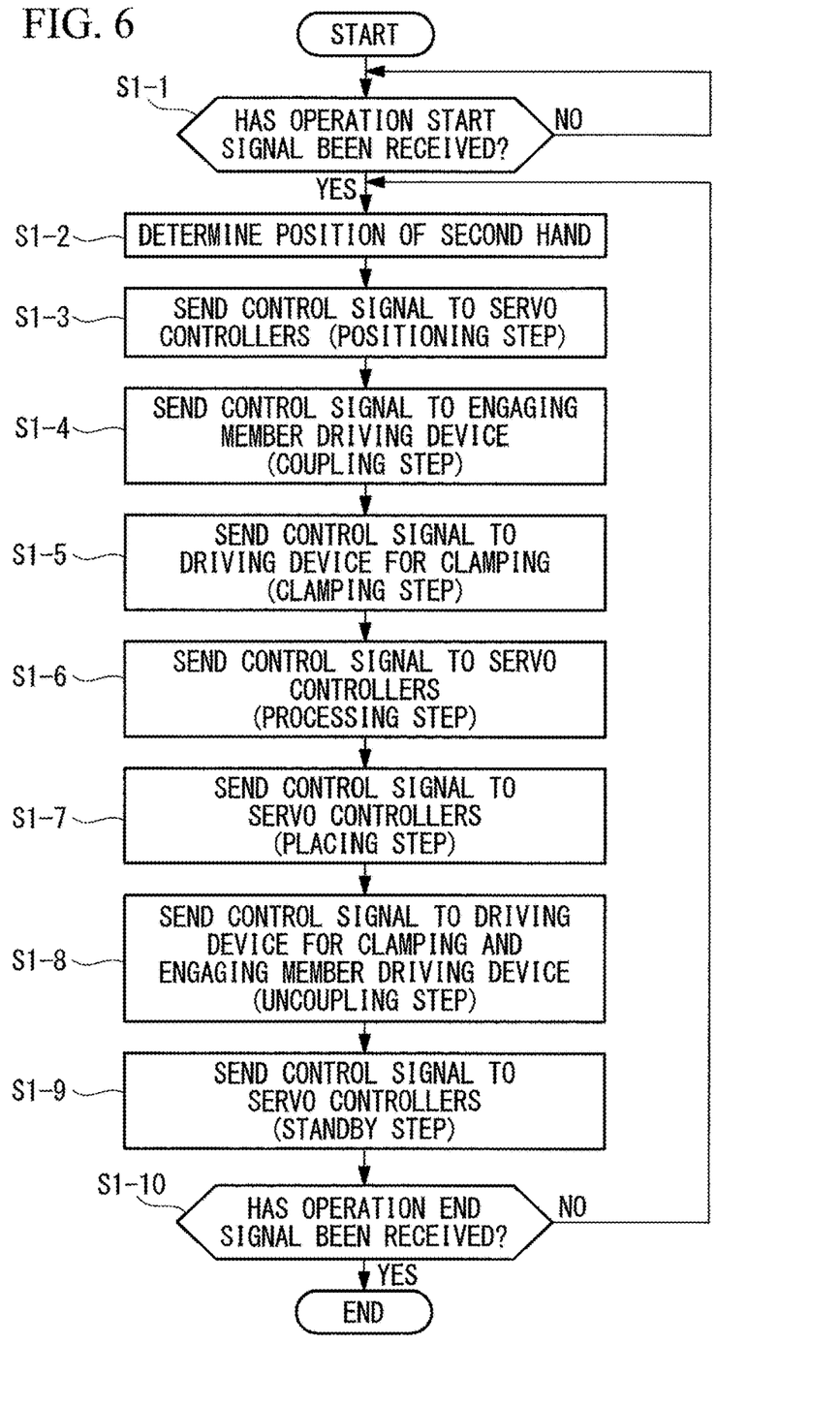
FIG. 6 is a flowchart showing operation of a control unit of the first embodiment.

As shown in FIG. 6, in this embodiment, when the robot control unit 30 receives a predetermined operation start signal (step S1-1), the controller 31 determines the position of the second hand 20, on which the workpiece W is placed, on the basis of a result of imaging by an imaging device 41 disposed above the table 40 (step S1-2). Then, the controller 31 sends a control signal to the servo controllers 33 so that the through-holes 16b of the first hand 10 are disposed above the guide shafts 22 of one of the second hands 20 in which the workpiece W is placed, and then sends a control signal to the servo controllers 33 so that the first hand 10 moves downward to a predetermined position in the Z-axis direction and the guide shafts 22 of the second hand 20 are inserted into the through-holes 16b of the first hand 10 (step S1-3).

Figure 7:
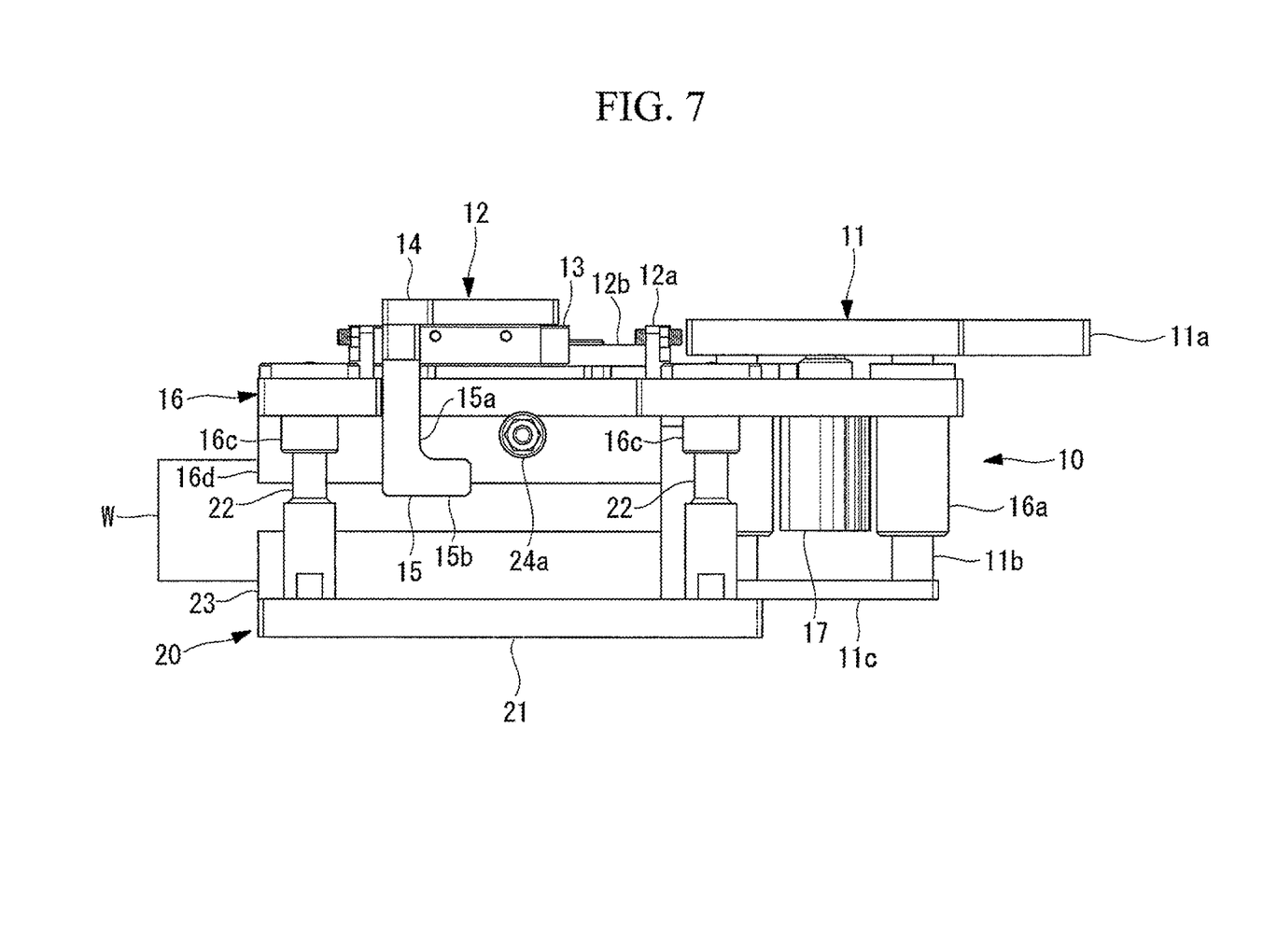
FIG. 7 is a view illustrating an action of the hand device of the first embodiment.

Thus, as shown in FIG. 7, the second hand 20 is positioned in the horizontal direction relative to the first hand 10 through the guide bushes 16c inside the through-holes 16b and the guide shafts 22. At this point, the first engaging member 14 is disposed at one side in the Y-axis direction.

Figure 8:
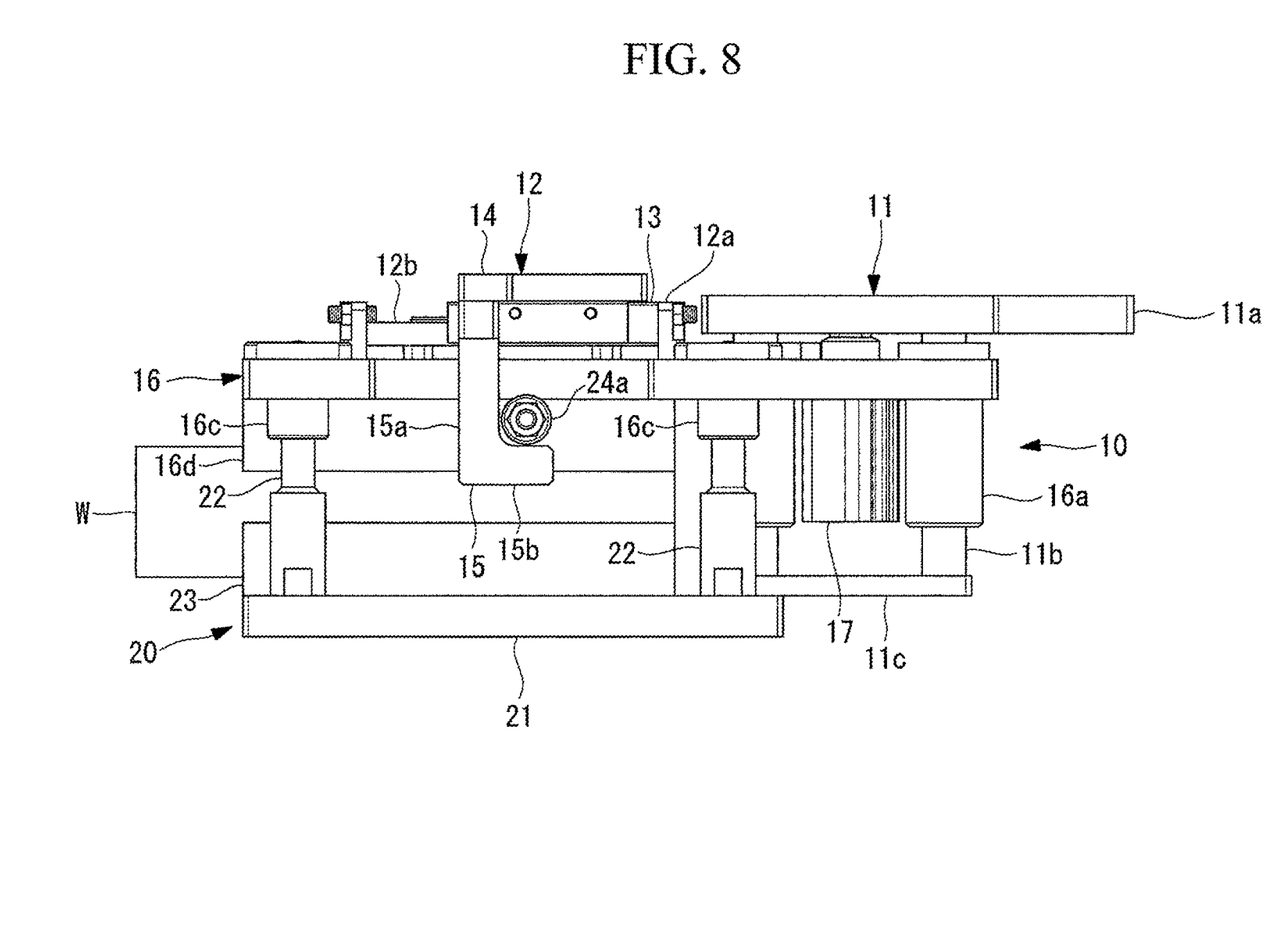
FIG. 8 is a view illustrating an action of the hand device of the first embodiment.

Next, the controller 31 sends a control signal to the engaging member driving device 13 so that the first engaging member 14 moves toward the other side in the Y-axis direction (step S1-4). Thus, as shown in FIG. 8, the horizontally extending portions 15b of the pair of engaging pieces 15 of the first engaging member 14 respectively engage with the engaging portions 24a of the pair of second engaging members 24 in the vertical direction, so that the second hand 20 is coupled to the first hand 10.

Figure 9:
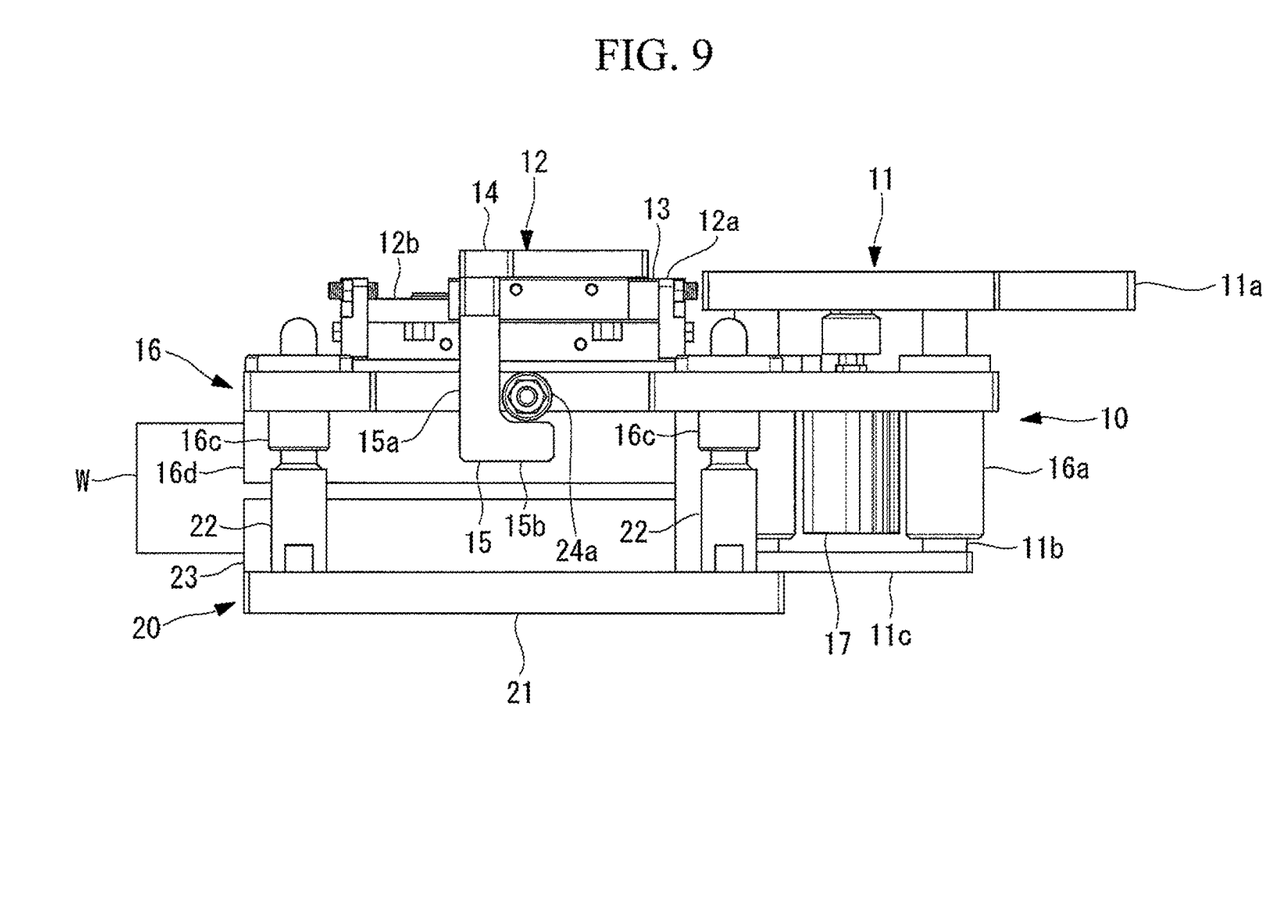
FIG. 9 is a view illustrating an action of the hand device of the first embodiment.

Next, the controller 31 sends a control signal to the driving device for clamping 17 so that the movable member 16 moves downward relative to the base 11 of the first hand 10 (step S1-5). Here, as the engaging pieces 15 of the first engaging member 14 and the engaging portions 24a of the second engaging member 24 are engaged with each other in the vertical direction, downward movement of the second hand 20 relative to the base 11 and the base member 12a of the first hand 10 is restricted. Accordingly, as shown in FIG. 9, when the movable member 16 moves downward relative to the base 11, the workpiece W is clamped between the movable member 16 and the workpiece stage 23 of the second hand main body 21. A workpiece pressing member 16d made of a plastic material, such as MC nylon, is provided on a lower surface of the movable member 16.

In this state, the controller 31 sends a control signal to the servo controllers 33 so that the first hand 10 to which the second hand 20 has been coupled moves toward a machine tool and a predetermined process is performed on the grabbed workpiece W by the machine tool (step S1-6).

Upon completion of the process, the controller 31 sends a control signal to the servo controllers 33 so that the second hand 20 is placed at a predetermined position in the table 40 (step S1-7). Then, the controller 31 sends a control signal to the driving device for clamping 17 so that the movable member 16 moves upward relative to the base 11, and sends a control signal to the engaging member driving device 13 so that the first engaging member 14 moves toward the one side in the Y-axis direction (step S1-8). Thus, the first hand 10 and the second hand 20 are uncoupled from each other.

Next, the controller 31 sends a control signal to the servo controllers 33 so that the first hand 10 is disposed at a predetermined standby position (step S1-9).

The controller 31 repeats step S1-2 to step S1-9 until a predetermined operation end signal is received (step S1-10).

In the first embodiment, the first hand 10 and the second hand 20 are positioned as the guide shafts 22 of the second hand 20 are inserted into the guide bushes 16c inside the through-holes 16b of the first hand 10. The first hand 10 and the second hand 20 are coupled together as the second engaging members 24 of the second hand 20 engage with the engaging pieces 15 of the first hand 10. Then, the movable member 16 of the first hand 10 is moved toward the second hand 20 to clamp the workpiece W. Thus, the workpiece W can be stably held during processing when the robot arm 2 is operated and the workpiece W is processed.

The hand device 1 can realize stable holding of the workpiece W by a simple configuration in that the first hand 10 and the second hand 20 are coupled together simply by moving the first engaging member 14 in the Y-axis direction in a state where the second hand 20 has been positioned relative to the first hand 10.

Moreover, the hand device 1 clamps the workpiece by moving a part of the first hand 10 toward the second hand 20 by the driving device for clamping 17, and therefore can stably generate a large clamping force.

A hand device 3 according to a second embodiment of the present invention will be described below with reference to the drawings.

Figure 10:
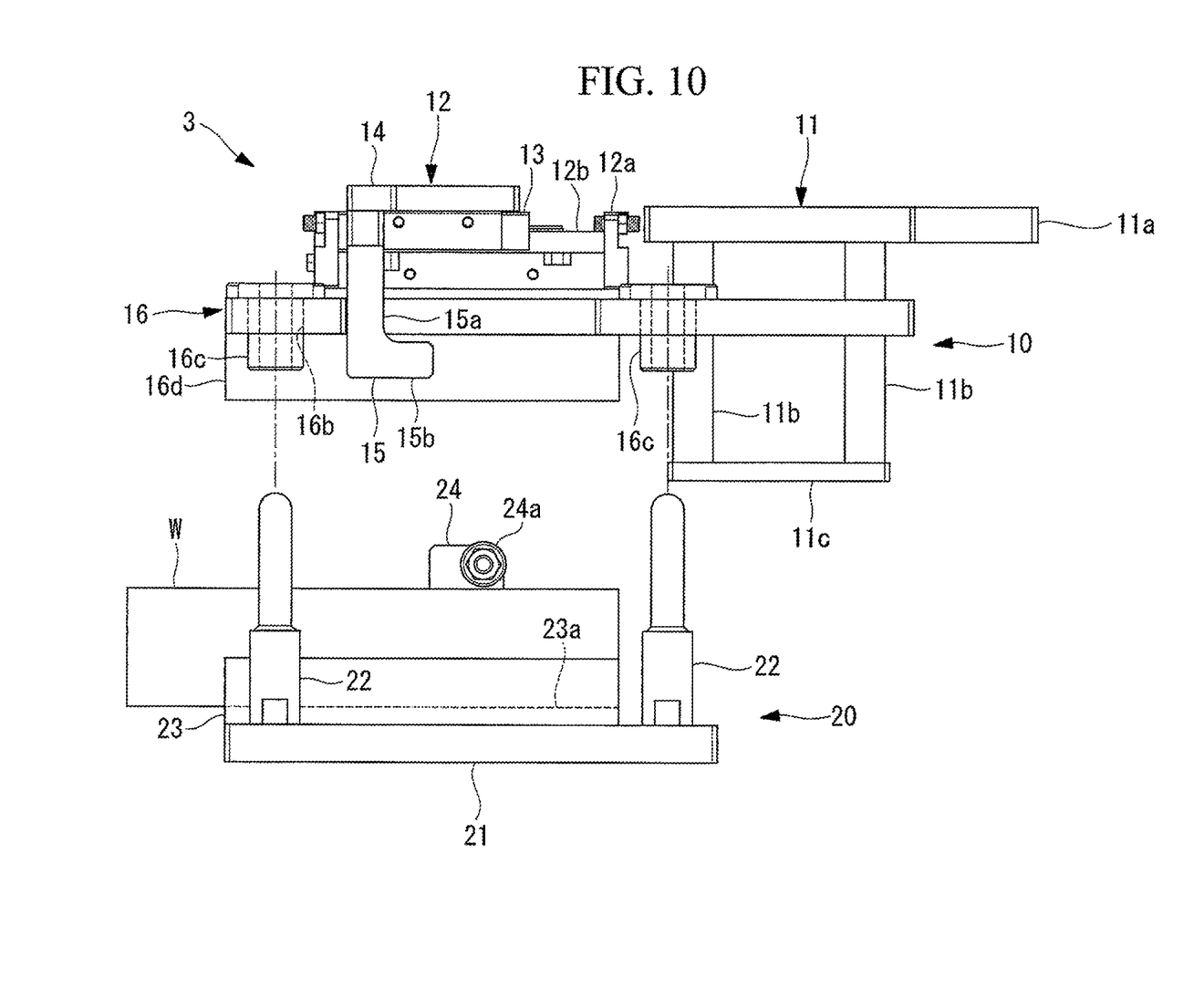
FIG. 10 is a front view of a hand device according to a second embodiment of the present invention.

As in the example shown in FIG. 10, the hand device 3 is different from the hand device 1 of the first embodiment in that the driving device for clamping 17 and the guide bushes 16a are omitted and that the workpiece pressing member 16d is immovably fixed to the fixed plate 11a. For example, the movable member 16 is fixed to the guide shafts 11b by welding etc., and thereby the movable member 16 as well as the base member 12a is fixed to the fixed plate 11a.

Figure 11:
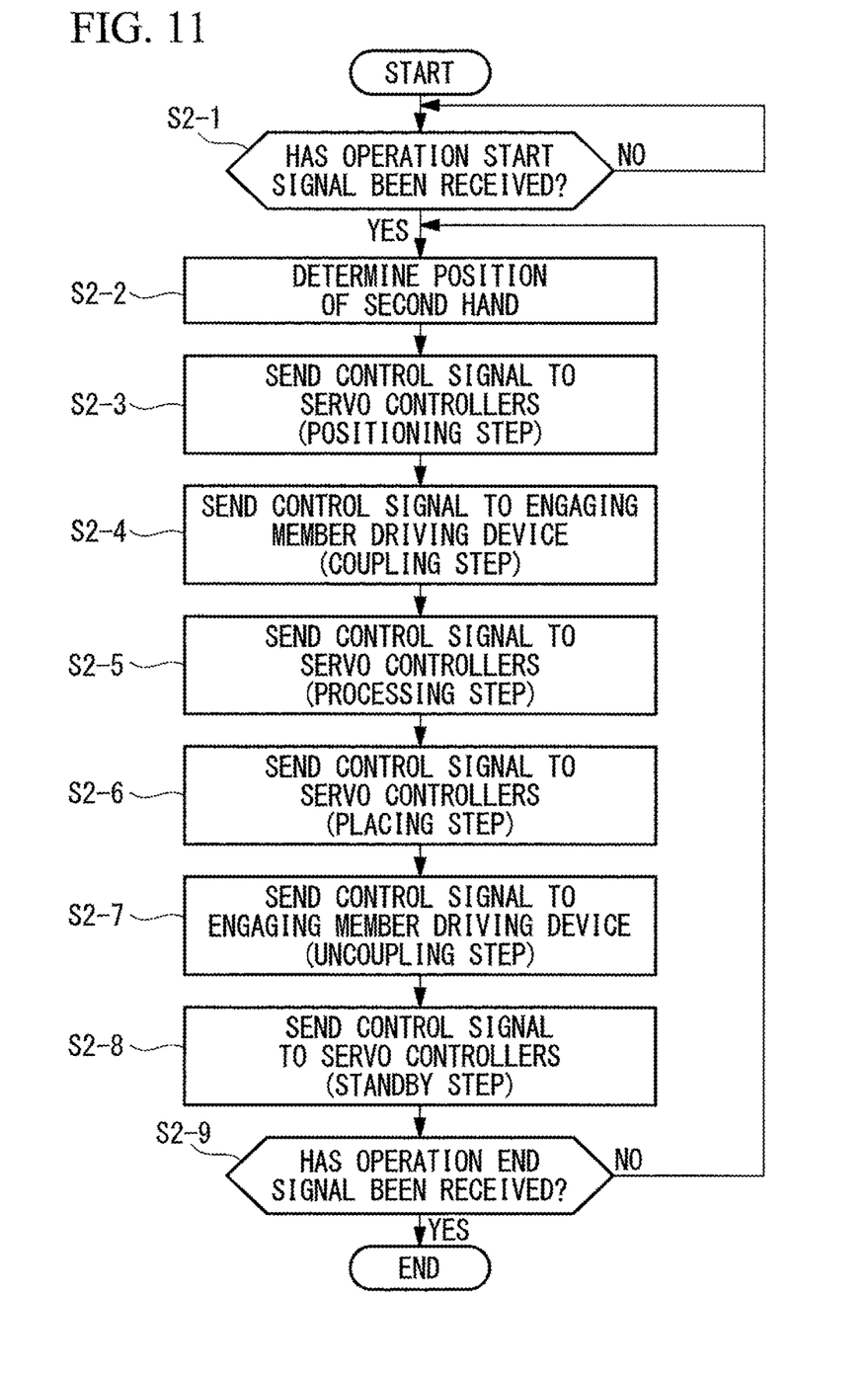
FIG. 11 is a flowchart showing operation of a control unit of the second embodiment.

Operation of the controller 31 of the robot control unit 30 in this case will be described. The controller 31 that is operated through the system program 32a sends a control signal to the servo controllers 33 and the engaging member driving device 13 in accordance with the retrieved operation program 32b. As shown in FIG. 11, when the robot control unit 30 receives a predetermined operation start signal (step S2-1), the controller 31 determines the position of the second hand 20, in which the workpiece W is placed, as in step S1-2 of the first embodiment (step S2-2).

Then, the controller 31 sends a control signal to the servo controllers 33 so that the through-holes 16b of the first hand 10 are disposed above the guide shafts 22 of one of the second hands 20 in which the workpiece W is placed, and then sends a control signal to the servo controllers 33 so that the first hand 10 moves downward to a predetermined position in the Z-axis direction and the guide shafts 22 of the second hand 20 are inserted into the through-holes 16b of the first hand 10 (step S2-3).

The predetermined position in the Z-axis direction is such a position that the workpiece W is clamped between the workpiece pressing member 16d of the first hand 10 and the workpiece stage 23 of the second hand 20, and that the clamping force is slightly larger than a force that is large enough to withstand the process performed by the machine tool. That is, the first hand 10 is pressed against the second hand 20 on the table 40 by the robot arm 2, and thereby the clamping force is generated. Alternatively, a force sensor that measures a clamping force can be provided, for example, between the mount 2b and the first hand 10, so that, while monitoring a measurement value of the force sensor, the controller 31 can move the first hand 10 downward until a predetermined clamping force is applied.

Figure 12:
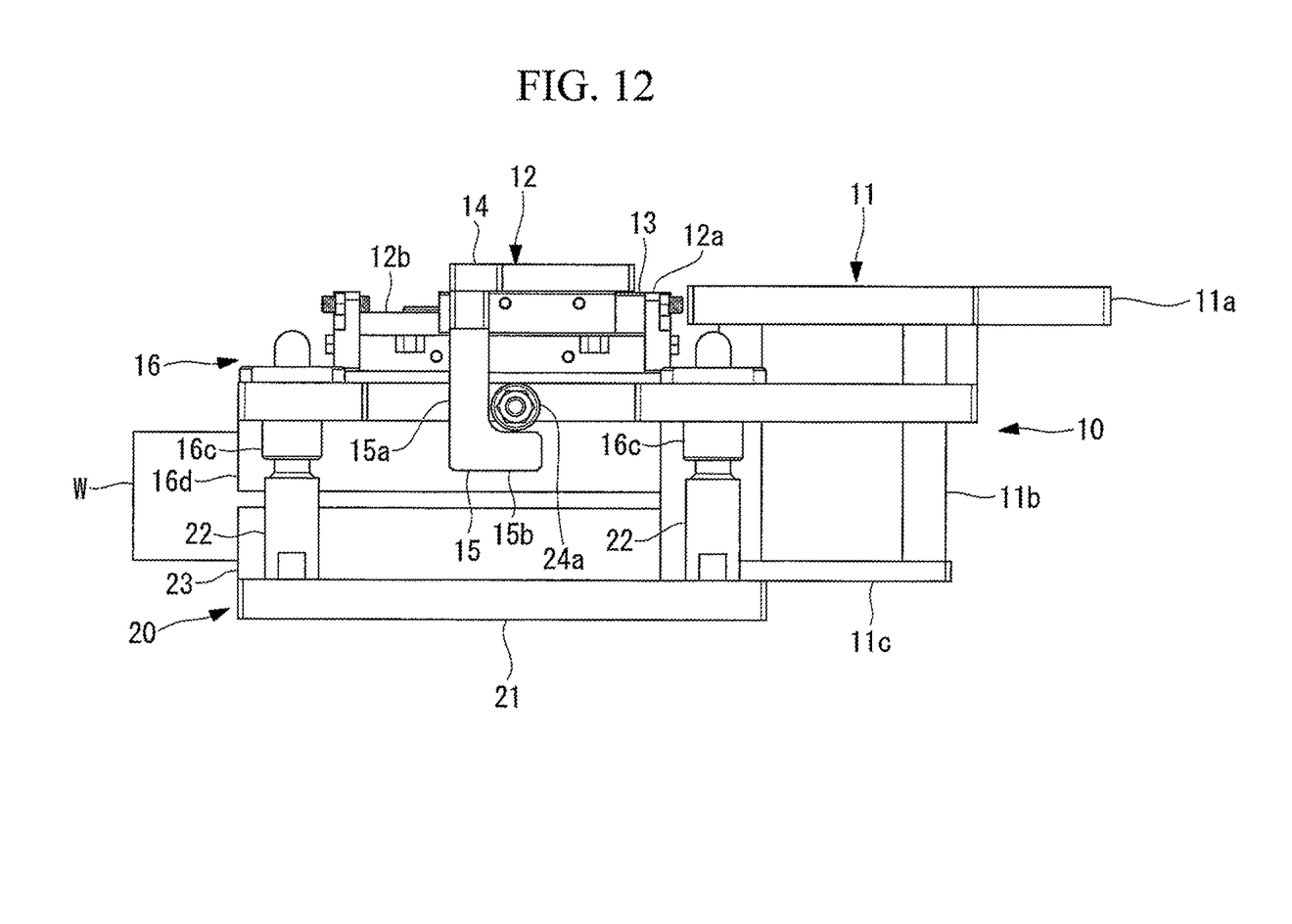
FIG. 12 is a view illustrating an action of the hand device of the second embodiment.

Next, the controller 31 sends a control signal to the engaging member driving device 13 so that the first engaging member 14 moves toward the other side in the Y-axis direction (step S2-4). Thus, as shown in FIG. 12, the horizontally extending portions 15b of the pair of engaging pieces 15 of the first engaging member 14 respectively engage with the engaging portions 24a of the pair of second engaging members 24 in the vertical direction, so that the second hand 20 is coupled to the first hand 10.

Here, it is preferable that a clearance between the horizontally extending portion 15b and the engaging portion 24a in the vertical direction be as small as possible when the two are positioned to be engaged with each other in the vertical direction in step S2-4.

Next, the controller 31 sends a control signal to the servo controllers 33 so that the first hand 10 to which the second hand 20 has been coupled moves toward the machine tool and a predetermined process is performed on the grabbed workpiece W by the machine tool (step S2-5).

At this point, the pressing force of the robot arm 2 is lost, so that the clamping force may become slightly smaller than that in step S2-3. However, this clamping force can well withstand the process performed by the machine tool, as the horizontally extending portions 15b and the engaging portions 24a are engaged with each other in the vertical direction.

Upon completion of the process, the controller 31 sends a control signal to the servo controllers 33 so that the second hand 20 is placed at a predetermined position in the table 40 (step S2-6).

Then, the controller 31 sends a control signal to the engaging member driving device 13 so that the first engaging member 14 moves toward the one side in the Y-axis direction (step S2-7). Thus, the first hand 10 and the second hand 20 are uncoupled from each other.

Next, the controller 31 sends a control signal to the servo controllers 33 so that the first hand 10 is disposed at a predetermined standby position (step S2-8).

The controller 31 repeats step S2-2 to step S2-8 until a predetermined operation end signal is received (step S2-9).

In the second embodiment, too, the first hand 10 and the second hand 20 are positioned as the guide shafts 22 of the second hand 20 are inserted into the guide bushes 16c inside the through-holes 16b of the first hand 10. The first hand 10 and the second hand 20 are coupled together as the second engaging members 24 of the second hand 20 engage with the engaging pieces 15 of the first hand 10. Then, the first hand 10 is pressed against the second hand 20 by the robot arm 2 to clamp the workpiece W, and the clamping force generated by this pressing is maintained by the first hand 10 and the second hand 20 being coupled together. Thus, the workpiece W can be stably held during processing when the robot arm 2 is operated and the workpiece W is processed.

In the first and second embodiments, a sufficient area in which the workpiece pressing member 16d of the first hand 10 and the workpiece stage 23 of the second hand 20 come in contact with the workpiece W can be secured, which is advantageous in improving the stability during processing.

Moreover, in the first and second embodiments, the plurality of second hands 20 are prepared and the workpiece W is placed in each second hand 20. This can, in some cases, eliminate the need to separately provide a dedicated table on which the workpieces W before being grabbed by the robot arm 2 are placed in a line, which is advantageous in reducing the cost.

To exchange the first hand 10 and the second hand 20 for other first hand 10 and second hand 20 according to the shape of the workpiece W, the second hand 20 on the table 40 can be moved by using the first hand 10 through the robot arm 2, which is also advantageous in reducing the cost.

The inventor has arrived at the following aspects of the present invention.

A hand device of a first aspect of the present invention includes: a first hand fixed to a robot arm; a second hand that has a workpiece stage on which a workpiece is to be placed and that is to be coupled to the first hand; a positioning mechanism that positions the second hand relative to the first hand when the second hand is coupled to the first hand; and a coupling mechanism capable of coupling the second hand having been positioned by the positioning mechanism to the first hand, and also capable of uncoupling the second hand from the first hand, wherein the hand device is configured to clamp the workpiece between the first hand and the second hand by moving at least a part of the first hand toward the second hand.

According to this aspect, the first hand and the second hand are positioned by the positioning mechanism and then coupled together, and at least a part of the first hand is moved toward the second hand to apply a clamping force to the workpiece. Thus, for processing, when the robot arm is operated and the workpiece is processed, this hand device can maintain the state where the first hand and the second hand are reliably coupled together and thereby stably hold the workpiece.

In the above aspect, it is preferable that the coupling mechanism has: a first engaging member provided in the first hand; a second engaging member provided in the second hand; and an engaging member driving device that is provided in the first hand and that moves the first engaging member in a predetermined direction to engage the first engaging member with the second engaging member in order to couple the second hand to the first hand in a state where the second hand has been positioned by the positioning mechanism.

Thus, this hand device can realize stable holding of a workpiece by a simple configuration in that the first hand and the second hand are coupled together simply by moving the first engaging member in a predetermined direction in a state where the second hand has been positioned relative to the first hand.

In the above aspect, it is preferable that the hand device further include a driving device for clamping that is provided in the first hand and that clamps the workpiece between the first hand and the second hand by moving a part of the first hand toward the second hand.

Thus, this hand device clamps a workpiece by moving a part of the first hand toward the second hand by the driving device for clamping, and therefore can stably generate a large clamping force.

According to the aforementioned aspects, a workpiece can be stably held during processing.

REFERENCE SIGNS LIST

1 Hand device
2 Robot arm
10 First hand
11 Base
12 Coupling mechanism
13 Engaging member driving device
14 First engaging member
15 Engaging piece
16 Movable member
17 Driving device for clamping
20 Second hand
21 Second hand main body
22 Guide shaft
23 Workpiece stage
24 Second engaging member
30 Robot control unit
40 Table
41 Imaging device
W Workpiece

The invention claimed is:

1. A hand device, comprising:
   a first hand fixed to a robot arm;
   a second hand that is not fixed to the robot arm and that has a workpiece stage on which a workpiece is to be placed and also that is to be coupled to the first hand;
   a positioning mechanism that positions the second hand relative to the first hand when the second hand is coupled to the first hand;
   a coupling mechanism capable of coupling the second hand having been positioned by the positioning mechanism to the first hand, and also capable of uncoupling the second hand from the first hand;
   wherein, due to the coupling, moving the first hand by the robot arm results in simultaneous movement of the workpiece and the second hand;
   wherein the hand device is configured to clamp the workpiece between the first hand and the second hand by moving at least a part of the first hand toward the second hand;
   wherein the coupling by the coupling mechanism restricts a movement of the first hand in a direction away from the second hand; and
   wherein the coupling mechanism comprises:
      a first engaging member provided in the first hand;
      a second engaging member provided in the second hand; and
      an engaging member driving device that is provided in the first hand and that moves the first engaging member in a predetermined direction to engage the first engaging member with the second engaging member in order to couple the second hand to the first hand in a state where the second hand has been positioned by the positioning mechanism.

2. A hand device, comprising:
   a first hand fixed to a robot arm;
   a second hand that is not fixed to the robot arm and that has a workpiece stage on which a workpiece is to be placed and also that is to be coupled to the first hand;
   a positioning mechanism that positions the second hand relative to the first hand when the second hand is coupled to the first hand;
   a coupling mechanism capable of coupling the second hand having been positioned by the positioning mechanism to the first hand, and also capable of uncoupling the second hand from the first hand;
   wherein, due to the coupling, moving the first hand by the robot arm results in simultaneous movement of the workpiece and the second hand;
   wherein the hand device is configured to clamp the workpiece between the first hand and the second hand by moving at least a part of the first hand toward the second hand;

wherein the coupling by the coupling mechanism restricts a movement of the first hand in a direction away from the second hand; and wherein the hand device further comprises a driving device for clamping, wherein the driving device is provided in the first hand and is configured to clamp the workpiece between the first hand and the second hand by moving a part of the first hand toward the second hand.

3. The hand device according to claim 2, wherein the first hand comprises a movable member that is supported by a plurality of guide shafts so as to be movable in a vertical direction relative to a base.

4. The hand device according to claim 3, wherein the driving device is fixed to the base.

5. The hand device according to claim 4, wherein the driving device comprises an air cylinder.

6. The hand device according to claim 4, wherein the driving device comprises a linear motor.

7. A hand device, comprising:
   a first hand fixed to a robot arm;
   a second hand that is not fixed to the robot arm and that has a workpiece stage on which a workpiece is to be placed and also that is to be coupled to the first hand;
   a positioning mechanism that positions the second hand relative to the first hand when the second hand is coupled to the first hand;
   a coupling mechanism capable of coupling the second hand having been positioned by the positioning mechanism to the first hand, and also capable of uncoupling the second hand from the first hand;
   wherein the hand device is configured to clamp the workpiece between the first hand and the second hand by moving at least a part of the first hand toward the second hand; and
   wherein the coupling by the coupling mechanism restricts a movement of the first hand in a direction away from the second hand;
   wherein the coupling mechanism comprises:
      a first engaging member provided in the first hand;
      a second engaging member provided in the second hand; and
      an engaging member driving device that is provided in the first hand and that moves the first engaging member in a predetermined direction to engage the first engaging member with the second engaging member in order to couple the second hand to the first hand in a state where the second hand has been positioned by the positioning mechanism.

8. The hand device according to claim 7, comprising a driving device for clamping, wherein the driving device is provided in the first hand and is configured to clamp the workpiece between the first hand and the second hand by moving a part of the first hand toward the second hand.

9. A hand device, comprising:
   a first hand fixed to a robot arm;
   a second hand that is not fixed to the robot arm and that has a workpiece stage on which a workpiece is to be placed and also that is to be coupled to the first hand;
   a positioning mechanism that positions the second hand relative to the first hand when the second hand is coupled to the first hand;
   a coupling mechanism capable of coupling the second hand having been positioned by the positioning mechanism to the first hand, and also capable of uncoupling the second hand from the first hand;
   a driving device for clamping, wherein the driving device is provided in the first hand and is configured to clamp the workpiece between the first hand and the second hand by moving a part of the first hand toward the second hand; and
   wherein the coupling by the coupling mechanism restricts a movement of the first hand in a direction away from the second hand.

10. The hand device according to claim 9, wherein the coupling mechanism comprises:
   a first engaging member provided in the first hand;
   a second engaging member provided in the second hand; and
   an engaging member driving device that is provided in the first hand and that moves the first engaging member in a predetermined direction to engage the first engaging member with the second engaging member in order to couple the second hand to the first hand in a state where the second hand has been positioned by the positioning mechanism.

* * * * *